United States Patent [19]
Kwiatek et al.

[11] Patent Number: 4,573,996
[45] Date of Patent: Mar. 4, 1986

[54] DEVICE FOR THE ADMINISTRATION OF AN ACTIVE AGENT TO THE SKIN OR MUCOSA

[75] Inventors: Alfred Kwiatek, New York, N.Y.; Jack W. Schwartz, Burlington, Vt.

[73] Assignee: Jonergin, Inc., Swanton, Vt.

[21] Appl. No.: 567,540

[22] Filed: Jan. 3, 1984

[51] Int. Cl.⁴ ............................................. A61L 15/06
[52] U.S. Cl. ................................................... 604/897
[58] Field of Search ............... 604/896, 897, 290, 289, 604/304, 307

[56] References Cited

U.S. PATENT DOCUMENTS

| | | | |
|---|---|---|---|
| 2,432,541 | 12/1947 | Peck | 604/307 |
| 3,797,494 | 3/1974 | Zaffaroni | 604/897 |
| 3,964,482 | 6/1976 | Gerstel et al. | 604/896 |
| 4,379,454 | 4/1983 | Campbell et al. | 604/897 |

Primary Examiner—John D. Yasko
Attorney, Agent, or Firm—Lerner, David, Littenberg, Krumholz & Mentlik

[57] ABSTRACT

A device is disclosed for administration of an active agent to a host, e.g., for transdermal administration. The device includes an impermeable adhesive layer which surrounds the permeable adhesive layer of the device and which with the outer surface layer of the device forms a pocket so that, when the device is adhered to the skin or mucosa, the active agent can be released to the skin or mucosa to provide a continuous dose of the active agent to the skin or mucosa but cannot permeate through the outer surface layer or radially outwardly through the active agent impermeable adhesive layer.

25 Claims, 8 Drawing Figures

DEVICE FOR THE ADMINISTRATION OF AN ACTIVE AGENT TO THE SKIN OR MUCOSA

BACKGROUND OF THE INVENTION

The present invention relates to a device for the administration of an active agent to a host. The device allows for topical administration to the host or administration through the skin or mucosa of the host over a period of time.

Transdermal administration systems are known in the art. For example, Ciba-Geigy's Transderm ®-Nitro and Transderm ®-V systems have been approved for transdermal administration of nitroglycerin and scopolamine, respectively.

Other similar devices are described, for example, in U.S. Pat. Nos. 3,598,122; 3,598,123; 3,734,097; 3,742,951; 3,797,494; 3,926,188; 3,996,934; 4,031,894; and 4,060,084.

Characteristically, the controlled continuous metering devices known before the present invention contained a backing member which defined the outer surface of the device, a membrane was sealed to the backing member and created a reservoir therebetween containing the active agent, and an active agent permeable adhesive layer on the membrane defined the other face surface. Alternatively, the active agent, rather than being in one separate reservoir, is contained in a plurality of microcapsules distributed throughout the permeable adhesive layer. In either case, the active agent is delivered continuously from the reservoir or microcapsules through a membrane into the active agent permeable adhesive, which contacts the skin or mucosa of the recipient.

In order to insure a constant, complete and continuous seal of the device to the skin or mucosa, and to insure the predetermined, controlled transport of the active agent to the skin or mucosa, the active agent permeable adhesive layer in the prior art devices has been made to extend substantially to the rim, or edge, of the surface of the backing member. Thus, in such devices, substantially the entire face, or surface, in contact with the skin or mucosa consisted of the active agent permeable adhesive. While such devices have a number of advantages, including a continuous seal, certain potential disadvantages are apparent.

For example, unless due care is exercised, contamination of the drug permeable adhesive layer can easily occur by finger contact when a user applies the device to the skin. Thus, where the fingers are sufficiently contaminated with perspiration, body oils and foreign matter, the resulting contamination of the active agent permeable adhesive may adversely affect the permeable nature and/or the adhering ability of the adhesive to the skin. This, in turn, can adversely affect the desired predetermined rate of transport of the active agent to the recipient.

Moreover, finger contact with the active agent permeable adhesive will contaminate the finger with the active agent. This is undesirable. For example, where the active agent is an eye irritant such as scopolamine, subsequent contact of the contaminated finger to the eye may result in irritation.

Further, since the active agent permeable adhesive is ordinarily present on the entire face in contact with the skin, the active agent and/or other formulation components may ooze from the sides, or rim, of the device, for example, during storage or during use.

SUMMARY OF THE INVENTION

It has now been found that a device can be provided which administers an active agent to the skin or mucosa of a host and which minimizes or avoids the above-discussed disadvantages of the prior art devices. The device of the invention is seepage resistant during use and storage and comprises an outer surface layer; and an inner surface layer comprised of an active agent permeable adhesive layer and an active agent impermeable adhesive layer, both of the active agent permeable and active agent impermeable layers being adapted to adhere to the skin or mucosa of a host. The active agent impermeable adhesive layer is connected to the outer surface layer (either directly or indirectly through another element of the device which is impermeable to the active agent), surrounds at least the perimeter of the active agent permeable adhesive layer and creates with the outer surface layer a pocket. The pocket includes at least on reservoir containing a membrane material separating such reservoir(s) from the active agent permeable adhesive layer so that, when the device is adhered to the skin or mucosa, the active agent can be released through the membrane and through the active agent permeable adhesive layer to the skin or mucosa to provide a continuous dose of the active agent to the skin or mucosa but cannot permeate through the outer surface layer or radially outwardly through the active agent impermeable adhesive layer.

The device of the present invention can provide an additional area of adhesion to assure firm contact of the device to the recipient's skin or mucosa without affecting the surface area of the skin (mucosa)/permeable adhesive layer interface which at least partially determines the dosage of the active agent which the device delivers during a specific period of time. Also, the device can provide a geometric design which is independent of the geometry of the skin (mucosa)/permeable adhesive layer interface. Moreover, the active agent present in the layer of permeable adhesive in the present invention is contained within the rim of the impermeable adhesive layer due to the presence of a barrier the latter layer creates, separating the active agent from the outer edge of the device, i.e., it prevents oozing during storage or use. Furthermore, because the rate of evaporation or diffusion of active agents is reduced, the present invention can provide improved storage life, especially for drugs having a significant volatility.

In one embodiment of the invention, the reservoir is formed from a backing member and a membrane sealed to the backing member so as to create the reservoir between the membrane and the backing member. The active agent permeable adhesive layer is on the membrane and is adapted to adhere to the skin or mucosa, and the active agent is contained in the reservoir. Preferably, the outer surface layer in such embodiment is an overlay covering layer which is coated on one surface with the active agent impermeable adhesive layer to create an impermeable adhesive surface. This impermeable adhesive surface has a sufficient surface area and is of a shape so that the impermeable adhesive surface overlaps completely the backing member. This impermeable adhesive surface is adhered to the backing member so that the impermeable adhesive surface provides the active agent impermeable adhesive layer which surrounds the perimeter of the active agent permeable adhesive layer and forms the pocket with the overlay covering layer.

In another embodiment of the invention including a reservoir formed between a backing member and the membrane as discussed above, the backing member is the outer surface layer and is impermeable to the active agent. In such embodiment, the backing member overlaps completely the membrane, and the active agent impermeable adhesive layer is connected at least to the overlapping portion of the backing member so that the active agent impermeable adhesive layer surrounds the perimeter of the active agent permeable adhesive layer.

In still another embodiment of the invention, the at least one reservoir is comprised of a plurality of microcapsules within the active agent permeable adhesive layer. The microcapsules contain the active agent encapsulated by the membrane material. Such active agent permeable adhesive layer is attached to the backing member so that it can adhere to the skin or mucosa.

The outer surface layer in this latter embodiment can be an overlay covering layer which is coated on one surface with the active agent impermeable adhesive layer to create an impermeable adhesive surface. As in the case described above, the impermeable adhesive surface has a sufficient surface area and is of a shape so that the impermeable adhesive surface overlaps completely the backing member and is adhered to the backing member so that the impermeable adhesive surface provides the active agent impermeable adhesive layer which surrounds the perimeter of the active agent permeable adhesive layer and forms the pocket with the overlay covering layer.

Alternatively, in this latter embodiment, the outer surface layer is the backing member which is impermeable to the active agent. The backing member is of a size and shape so that it completely overlaps the active agent permeable adhesive layer containing the microcapsules. The active agent impermeable adhesive layer is attached at least to the overlapping portion of the backing member so that the active agent impermeable adhesive layer surrounds the perimeter of the active agent permeable adhesive layer and with the backing member forms the pocket.

BRIEF DESCRIPTION OF THE DRAWING

A more complete appreciation of the invention and many of its attendant advantages can be readily attained by reference to the following detailed description when considered in connection with the following drawings, wherein.

It should be noted that the drawings are not necessarily to scale, but that certain elements have been expanded to show more clearly the various aspects of the present invention and their advantages.

DETAILED DESCRIPTION OF THE INVENTION

Figure 1:
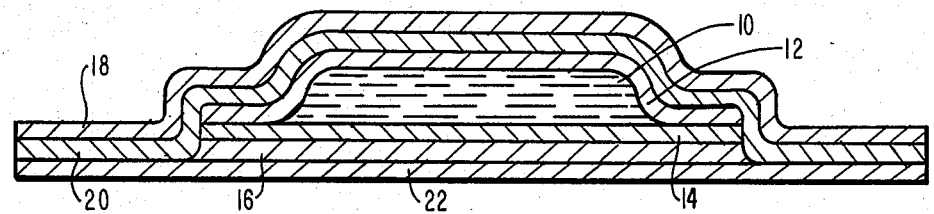
FIG. 1 shows a cross-sectional view of a preferred device according to the present including an overlay covering layer.

Referring now to the drawings (in which like numerals are used to identify similar elements in the various embodiments), FIG. 1 shows a preferred construction of the device according to the present invention. The active agent is contained in a separate and distinct reservoir 10 created by a backing member 12 and a membrane 14 sealed to each other about the circumference or perimeter of the membrane. An active agent permeable adhesive layer 16 is applied to the surface of the membrane opposite the reservoir 10. An overlay covering layer 18 has a layer 20 of an active agent impermeable adhesive on one surface thereof. The overlay covering layer 18 and the applied active agent impermeable adhesive layer 20 have a sufficient surface area and are of a shape so that, when they are attached to the backing member 12, they overlap the backing member 12 completely. Thus, the impermeable adhesive surface adheres to the backing member so that the active agent impermeable adhesive layer 20 surrounds at least the perimeter of the active agent permeable adhesive layer 16. The active agent permeable adhesive layer 16 and the active agent impermeable adhesive layer 20 are positioned so that, when the protective liner 22 (e.g., a silicone release coated polyethylene terephthlate film) is removed, the two adhesive layers can be applied to the skin or mucosa. The overlay covering layer 18 and the impermeable adhesive layer 20 thus form a pocket surrounding the backing member 12, the reservoir 10, the membrane 14 and the active agent permeable adhesive layer 16 so that, when the device is adhered to the skin or mucosa, the active agent can be released through the membrane 14 and through the active agent permeable adhesive layer 16 to provide a continuous dose of the active agent therethrough but cannot permeate through the outer surface layer 18 or radially outwardly through the active agent impermeable adhesive layer 20.

Figure 2:
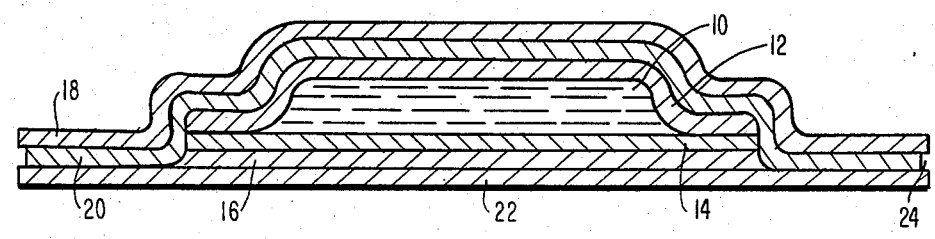
FIG. 2 shows a cross-sectional view of a similar embodiment of the present invention, including a tab for easy removal of a protective liner from the device.

The embodiment shown in FIG. 2 differs from that in FIG. 1 only in that the overlay covering layer 18 overlaps the active agent impermeable adhesive layer 20 to provide a tab 24 for easy removal of the protective liner 22 from the remainder of the device. This tab need not be around the entire periphery of the device, but may be limited to only one portion of the overlay covering layer 18.

Figure 3:
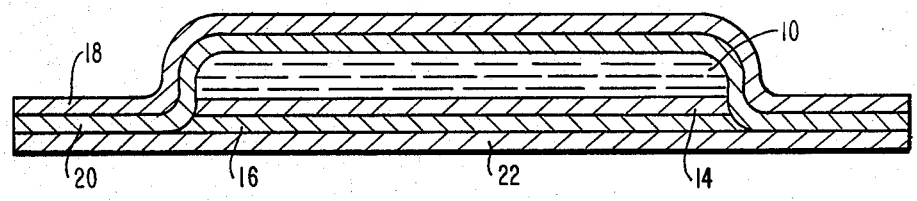
FIG. 3 shows a cross-sectional view of another embodiment of the present invention without a backing member.

The embodiment shown in FIG. 3 is somewhat similar to that shown in FIG. 1. However, in the device shown in FIG. 3, there is no backing member. Rather, the reservoir 10 is created in the space between the active agent impermeable adhesive layer 20 and the membrane 14 to which the active agent impermeable adhesive layer 20 is attached at the perimeter of the membrane.

Figure 4:
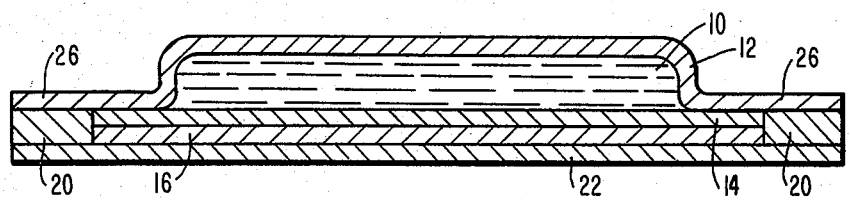
FIG. 4 shows a cross-sectional view of another embodiment of the invention in which the outer surface layer is a backing member.
Figure 5:
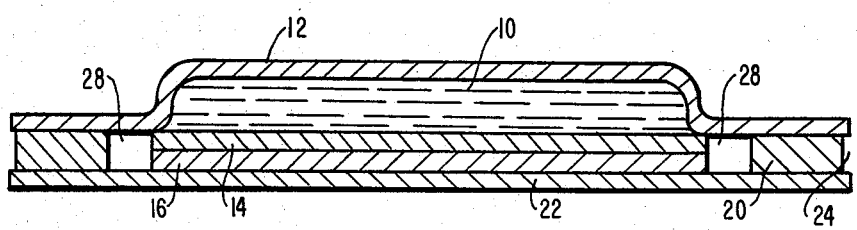
FIG. 5 shows a cross-sectional view of an embodiment of the invention similar to that shown in FIG. 4 but including a tab for removal of a protective liner and a gap between the permeable and impermeable adhesive layers.
Figure 6:
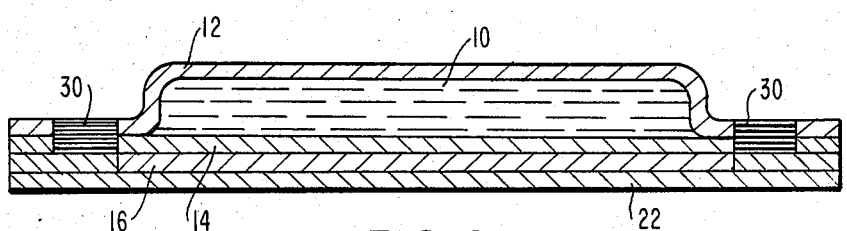
FIG. 6 shows a cross-sectional view of still another embodiment of the invention in which the membrane is heat sealed to the backing member along a line about the reservoir for the active agent to create an active agent impermeable seal along the line.

Another embodiment of the present invention is shown in FIGS. 4, 5, and 6 in which an overlay covering layer 18 is not employed. Rather, the backing member 12 is impermeable to the active agent and performs the function of the outer surface layer of the device.

In the embodiment shown in FIG. 4, the membrane 14 is sealed to the backing member 12 so as to create a reservoir 10 containing the active agent therebetween. On the surface of the membrane 14 opposite the reservoir 10, the active agent permeable adhesive layer 16 is applied. The backing member 12 extends outwardly from the periphery of the membrane 14 and from the active agent permeable adhesive layer 16. Thus, the backing member 12 overlaps completely the membrane 14 and the active agent permeable adhesive layer 16. The active agent impermeable adhesive layer 20 is attached to this overlapping portion 26 of the backing member 12 so that the active agent impermeable adhesive layer 20 surrounds the perimeter of the active agent permeable adhesive layer 16 and with the backing member 12 forms the pocket which prevents seepage of the active agent from the device during storage or use.

The embodiment shown in FIG. 5 is similar to that shown in FIG. 4. However, in this instance a tab 24 is created for easy removal of the protective liner 22 by having the backing member 12 extend (at least on one portion thereof) radially outwardly from the active agent impermeable adhesive layer 20 attached thereto. The gap 28 shown in FIG. 5 illustrates that the active agent impermeable adhesive layer 20 need not directly contact in all instances the active agent permeable adhesive layer 16 and/or membrane 14.

As shown in FIG. 6, the active agent impermeable adhesive layer 20 also need not be directly attached to the backing member 12. In this instance as shown in FIG. 6, the membrane material 14 extends radially outwardly to the outer periphery of the backing member 12. The membrane 14 is heat sealed to the backing member along a circumferential or peripheral line so as to create a seal 30 which is impermeable to the active agent contained in the reservoir created between the backing member 12 and the membrane 14. The active agent impermeable adhesive layer 20 in this embodiment is thus indirectly connected to the outer surface member (here the backing member 12) by attachment to the membrane 14 at least along the line created by the impermeable heat seal 30. The active agent permeable adhesive layer 16 is attached to the membrane 14 in such a manner so that the active agent impermeable adhesive layer 20 completely surrounds the perimeter of the active agent permeable adhesive layer. Thus in this instance, the impermeable adhesive layer 20, the impermeable heat seal 30 and the impermeable backing member 12 form the above discussed pocket to prevent seepage.

Figure 7:
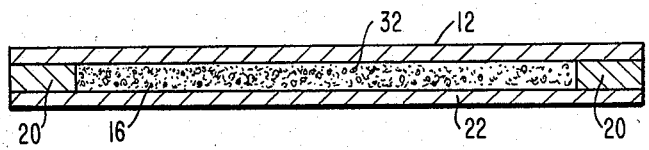
FIG. 7 shows a cross-sectional view of still another embodiment of the invention in which the active agent is contained in microcapsules within the active agent permeable adhesive layer.

The embodiment shown in FIG. 7 illustrates a device in accordance with the present invention in which the active agent is contained in microcapsules 32 within the active agent permeable adhesive layer 16 of the device. The microcapsules 32 are comprised of membrane material containing the active agent therein. As shown in FIG. 7, the permeable adhesive layer 16 containing the microcapsules is attached to the backing member 12. The backing member 12, however, extends radially outwardly from the outer perimeter of the permeable adhesive layer 16. Around the outer perimeter of the permeable adhesive layer 16 containing the microcapsules, the impermeable adhesive layer 20 is attached to the backing member 12. Thus, in this instance, the impermeable adhesive layer 20 and the backing member 12 form the pocket discussed above.

Figure 8:
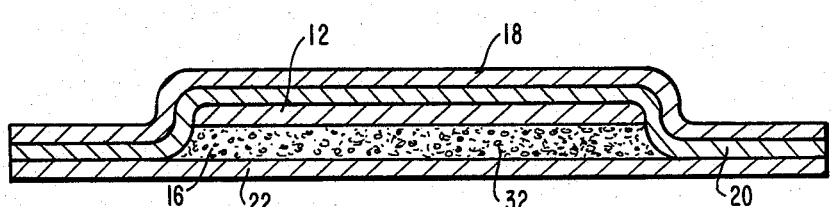
FIG. 8 shows a cross-sectional view of an embodiment of the invention similar to that of FIG. 9 but including an overlay covering layer.

As shown in FIG. 8, another embodiment having the active agent contained in microcapsules 32 within the permeable adhesive layer 16 includes an overlay covering layer 18. In this embodiment, the permeable adhesive layer 16 containing the microcapsules 32 is attached to the backing member 12. An overlay covering layer 18 having on one surface thereof the active agent impermeable adhesive layer 20 is laid over the backing member 12 so that the impermeable adhesive layer 20 surrounds at least the perimeter of the permeable adhesive layer 16. The overlay covering layer 18 and the impermeable adhesive layer 20, in this instance, again form the seepage resistent pocket discussed above.

The outer surface member, be it an overlay covering layer or a backing member as described above, is preferably a thin film or sheet. In many instances, because of the area of skin to which the device is to be attached the device is flesh colored for cosmetic reasons. The outer surface layer normally provides support and a protective covering for the device.

The outer surface layer is preferably made of a material or combination of materials which is substantially impermeable to the layer or layers with which it can be in contact, i.e., to the active agent, the impermeable and permeable adhesives, etc. However, a primary purpose is to prevent seepage of the active agent through the outer surface layer of the device so, if the outer surface layer is coated on the surface in contact with the remainder of the device with the active agent impermeable adhesive layer, this impermeable adhesive layer will perform this purpose even if the outer surface layer is not totally impermeable to the active agent. Thus, it is not necessary in all instances that the outer surface layer be impermeable to the active agent, although in most instances it normally is. By substantially impermeable we mean that the other components in contact with the layer or component under consideration will not appreciably permeate through such layer or component for the normal period of use and storage of the device, see the discussion of impermeability, infra.

The actual material used for the outer surface layer, i.e., the overlay covering layer and/or the backing member, will depend on the properties of the materials in contact therewith. Some suitable materials for the outer surface layer include, for example, cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride, paper, cloth, and aluminum foil. The material may advantageously be porous in order to permit the transfer of air.

The material which forms the outer surface layer, either the overlay covering layer or the backing member, may be flexible or non-flexible. Preferably, a flexible outer surface layer is employed to conform to the shape of the body member to which the device is attached.

Preferably, the material which forms the overlay covering layer and/or the backing member is a film or a composite of films. The composite can be a metallized (e.g., aluminized) film or a laminate of two or more films or a combination thereof. For example, a laminate of polyethylene terephthalate and polyethylene or a polyethylene/metallized polyethylene terephthalate/polyethylene laminate can be employed. The preferred polymers include polyethylene, polypropylene, polyvinyl chloride and polyethylene terephthalate.

As mentioned above, a primary purpose of the active agent impermeable adhesive layer is to provide adhesion to the skin or mucosa and to prevent seepage of the active agent from the device during storage and use. Thus, any adhesive which performs these functions will be suitable for use in the present invention. The degree of impermeability of the active agent impermeable adhesive layer to the active agent will vary depending upon the active agent, carrier, transporting agent, etc. Preferably, the active agent impermeable adhesive layer is a pressure sensitive adhesive suitable for contact with the skin or mucosa, e.g., dermatologically acceptable. Examples of suitable pressure sensitives for use in the present invention as the active agent impermeable adhesive layer include natural rubber adhesives such as R-1072 from B. F. Goodrich Co., No. 735 from C. L. Hawthaway, and No. 5702 from Evans-St. Clair; acrylic adhesives such as PS-41 from C. L. Hawthaway, VR-0833 from H. B. Fuller, Adcote 73A207A from Morton Chemical, Nos. 80-2404, 80-1054, 72-9056, and 72-9399 from National Starch, Nos. E-2015, E-2067 and E-1960 from Rohm & Haas, M-6112 from Uniroyal Inc. and Daratak 74 L from W. R. Grace; and synthetic rubber adhesives such Jowatherm 270-00 and Jowatherm S-3202 from Jowat Corp. and 70-9416 from National Starch.

The width and thickness of the impermeable adhesive layer for contact with the skin or mucosa is that width and thickness which provides at least sufficient impermeability to the active agent (and if necessary to the other components of the device with which the impermeable adhesive layer is in contact) so that the active agent does not seep out of the device as explained above. Some suitable widths include 1/16 to 2 inches, and preferably, ⅛ to 1 inches. In most instances, the width will be ¼ to ½ inch depending on the specific use. The width and thickness need not be uniform and may vary around the perimeter of the device, e.g., to provide a specific geometric shape or to provide a tab for removal of a protective liner.

The active agent permeable adhesive layer also joins the device to the skin or mucosa of the host. Therefore, the adhesive is preferably dermatologically acceptable. The active agent permeable adhesive layer is also preferably a pressure-sensitive adhesive. Any of the well-known, dermatologically acceptable, pressure-sensitive adhesives which permit drug migration therethrough can be used in the present invention. Some suitable permeable adhesives include acrylic or methacrylic resins such as polymers of esters of acrylic or methacrylic acid (e.g., n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol esters thereof), alone or copolymerized with ethylenically unsaturated monomers such as acrylic acid, methacrylic acid, acrylamide, methacrylamides, N-alkoxymethyl acrylamides, N-alkoxymethyl methacrylamides, N-t-butylacrylamide, itaconic acid, vinyl acetate, N-branched alkyl maleamic acids wherein the alkyl group has 10 to 24 carbon atoms, glycol diacrylates, or mixture of these; natural or synthetic rubbers such as silicon rubber, styrene-butadiene rubber, butyl-ether rubber, neoprene rubber, nitrile rubber, polyisobutylene, polybutadiene, and polyisoprene; polyurethane elastomers; vinyl polymers, such as polyvinyl alcohol, polyvinyl ethers, polyvinyl pyrrolidone, and polyvinyl acetate; ureaformaldehyde resins; phenol formaldehyde resins; resorcinol formaldehyde resins; cellulose derivatives such as ethyl cellulose, methyl cellulose, nitrocellulose, cellulose acetatebutyrate, and carboxymethyl cellulose; and natural gums such as guar, acacia, pectina, starch, destria, gelatin, casein, etc. The adhesives may be compounded with tackifiers and stabilizers as is well-known in the art.

The permeable adhesive layer preferably contains some of the active agent when the device is placed on the skin. This provides an initial drug presence at the skin or mucosa and eliminates delay in absorption of the active agent or in topical application, if that is desired. Thus, the drug is immediately available to the host. The initial drug presence may be due to the permeations through the membrane and/or to an amount of the drug mixed in with active agent permeable adhesive layer during manufacture.

The amount of the active agent present in the permeable adhesive layer depends on the initial drug presence desired, e.g., for a pulse dosage. For example, U.S. Pat. No. 4,031,894 discloses that 10-200 micrograms scopolamine base per $cm^2$ effective surface area is a suitable initial amount of active agent in the permeable adhesive layer.

The width and thickness of the permeable adhesive layer for contact with the skin or mucosa is that width and thickness which provides sufficient permeability to the active agent and a suitable surface area to allow the dosage rate desired to the skin or mucosa. These widths and thicknesses are conventional in the art and therefore need not be discussed in detail here.

In most instances, the impermeable adhesive layer will extend to the outer rim of the device. However, as pointed out above, the backing member or overlay covering layer may extend radially outwardly past the impermeable adhesive layer to provide a tab for removal of the protective liner from the remainder of the device for application of the device to the skin or mucosa. Also, the impermeable adhesive layer is in most instances in direct contact and/or adjacent to the permeable adhesive layer. However, this is not necessary and there may be a gap between the permeable adhesive layer and the impermeable adhesive layer if desired, e.g., see FIG. 5.

The thicknesses and shapes of the permeable and impermeable adhesive layers in the device of the present invention need not be the same or correspond. This is a particular advantage to the invention in that the device can be made to adhere to specific portions of the skin or mucosa by primary means of the impermeable adhesive layer while not affecting the surface area of the permeable adhesive layer through which the active agent passes, (i.e., the shape of the device can be varied without varying the surface area of the membrane and permeable adhesive layer which determines the amount of active agent delivered to the skin or mucosa).

As explained above, the reservoir containing the active agent can exist as a single separate reservoir, e.g., as in the embodiments shown in FIGS. 1-6, or as a plurality of microcapsules in the permeable adhesive layer containing the active agent, e.g., as in the embodiments shown in FIGS. 7 and 8. In either case, the reservoir serves as the storage area for the active agent, e.g., as is described in U.S. Pat. No. 4,031,894.

The reservoir is separated from the permeable adhesive layer by a membrane. The membrane may be microporous in which case the pores become filled with active agent from the reservoir. The membrane may also function in any other way as long as the active agent permeates through the membrane at a suitable rate. The membrane and the permeable adhesive layer can be monolithic. In this instance, the surface of the membrane is treated to make it adhesive in nature so that it will adhere to the skin or mucosa but still provide membrane permeability characteristics.

The suitability of the rate of permeation of the active agent through the membrane depends on the desired dosage rate the permeability of the active agent through the skin or mucosa, if transdermal type administration is desired. An effective amount of the active agent is contained in the reservoir to provide the desired dosage. Sometimes, the skin or mucosa itself determines the rate at which the active agent will be administered therethrough. In these latter instances, if the dosage rate through the skin or mucosa is the dosage rate desired, the membrane need not provide any limiting rate of permeation function but need only supply sufficient active agent to the skin or mucosa to allow the desired permeation through the skin or mucosa which itself determines the dosage rate at which the active agent will be absorbed by the host.

As one example, the flux of scopolamine through the membrane in the device disclosed in U.S. Pat. No. 4,031,894 is such that scopolamine is released from a reservoir to the skin at a constant rate in the range of 0.3–15 micrograms per hour. Membranes suitable for use in devices which so dispense scopolamine are said in U.S. Pat. No. 4,031,894 to have porosities from about 0.1–0.5, tortuosities from 1–10, and thicknesses from $10^{-3}$ to $10^{-2}$ centimeters.

When distributed through the permeable adhesive layer in microcapsules such as shown in FIGS. 7 and 8, the active agent is encapsulated with a membrane material permeable to passage of the drug, e.g., as described in U.S. Pat. No. 3,734,097. The encapsulating membrane is made of a material through which the active agent permeates at the desired rate, e.g., a predetermined, controlled rate. The microcapsules generally are substantially spherical in shape and may have any suitable diameter.

The materials suitable for use as the membrane are conventional in the art and need not be discussed in detail here. Some preferred materials for a separate membrane layer may be, for example, polypropylene, polycarbonates, polyvinyl chloride, cellulose acetate, cellulose nitrate, and polyacrylonitrile. Some suitable encapsulating membrane materials include, for example, hydrophobic polymers such as polyvinyl chloride either unplasticized or plasticized with long-chain fatty amides or other plasticizers, plasticized nylon, unplasticized soft nylon, silicone rubber, polyethylene, and polyethylene terephthalate. Hydrophilic polymers can also be employed such as esters of acrylic and methacrylic acid (e.g., as described in U.S. Pat. Nos. 2,976,576 and 3,220,960 and Belgium Pat. No. 701,813); modified collagen; cross-linked hydrophilic polyether gels (e.g., as described in U.S. Pat. No. 3,419,006); cross-linked polyvinyl alcohol; cross-linked partially hydrolyzed polyvinyl acetate; cellulosics such as methyl cellulose, ethyl cellulose, and hydroxyethyl cellulose; and gums such as acacia, carboxymethylcellulose, and carageenan alone or combined with gelatin.

Any of the conventional encapsulation techniques known in the prior art can be used to prepare the microcapsules for the present invention. Some suitable methods are disclosed in U.S. Pat. No. 3,734,097.

The rate of permeation of the active agent through the membrane of the reservoir or of the microcapsules depends on factors such as the affinity of the active agent for the membrane and the thickness of the membrane. Therefore, the appropriate membrane material and its thickness depend on the active agent used, the nature of any carriers and transporting agents, and the desired rate of permeation. The selection of the membrane and of its thickness provides a means, if desired, for controlling the dosage rate to the skin or mucosa.

In most instances, the impermeable adhesive layer is in direct contact with the outer surface layer, either the backing member and/or the overlay covering layer, to create the pocket to prevent seepage of the active agent from the device. However, in instances where the backing member is heat sealed to the membrane so that the active agent cannot seep radially outwardly through the membrane through the heat seal, the impermeable adhesive layer may be in contact with this heat sealed portion of the membrane so as to create the pocket.

The active agents suitable for use in the present invention may be, for example, systemic or topical drugs. Individual active agents or mixture thereof, if desired, can be employed. Any drug which passes through the skin or mucosa can be employed for internal administration in the device of the invention, so long as the drug will pass through the permeable adhesive layer and the material forming the membrane or microcapsules.

Suitable systemic drugs for administration by the claimed device include those useful in treating emesis and nausea as is described in U.S. Pat. No. 4,031,894, e.g., preferably, scopolamine.

Other suitable drugs include the coronary vasodilators described in U.S. Pat. No. 3,742,951 such as compounds having nitrate moiety. Some suitable coronary vasodilators include organic and inorganic nitrates such as amyl nitrate, nitroglycerin (glyceryl trinitrate), sodium nitrate, erythrityl tetranitrate, pentaerythritol tetranitrate, isosorbide dinitrate, mannitol hexanitrate, trolnitrate phosphate (triethanolamine biphosphate), and the like. Nitroglycerine is a preferred coronary vasodilator. Also suitable are the beta adrenegic blocking drugs such as propranolol.

Still other suitable systemic drugs are disclosed in U.S. Pat. No. 3,996,934 and include anti-microbial agents such as penicillin, tetracycline, oxytetracycline, chlortetracycline, chloramphenicol, and sulfonamides; sedatives and hypnotics such as pentabarbital sodium, phenobarbital, secobarbital sodium, codeine, (-bromoisovaleryl)urea, carbromal, and sodium phenobarbital; psychic energizers such as 3-(2-aminopropyl)indole acetate and 3-(2-aminobutyl)indole acetate; tranquilizers such as reserpine, chlorpromazine hydrochoride, and thiopropazate hydrochloride; hormones such as adrenocorticosteroids, for example, 6-methylprednisolone; androgenic steroids, for example, methyltestosterone, and fluoxymesterone; estrogenic steroids, for example, estrone, 17 beta-estradiol and ethinyl estradiol; progestational steroids, for example, 17-hydroxyprogesterone acetate, medroxyprogesterone acetate, 19-norprogesterone, and norethindrone; thyroxine; antipyretics such as aspirin, salicyclamide, and sodium salicylate;

morphine and other narcotic analgesics; antidiabetics, e.g. insulin; cardiovascular agent, e.g., nitroglycerin as discussed above, and cardia glycosides such as digitoxin, digoxin, ouabain; antispasmodics such as atropine, methscopolamine bromide, methscopolamine bromide with phenobarbital; antimalarials such as the 4-ammoquinolines, 9-aminoquinolines, and pyrimethamine; and nutritional agents such a vitamins, essential amino acids, and essential fats.

Some examples of topical drugs suitable for use in the present invention include, for example, the folic acid antagonists, anti-neoplastic agents, and antimitotic agents described in U.S. Pat. No. 3,734,097. Some suitable examples of folic acid antagonists include, for example, methotrexate, aminopterin, 3'-chloromethotrexate and 3',5'-dichloromethotrexate. Some anti-neoplastic agents include, for example, vincristine, vinblastine, 5-fluorouracil, 5-fluorodeoxyuridine, and 6-mercaptopurine. Some antimitotic agents include, for example, colchicine and podophyllum.

The active agents suitable for use in this invention may be present in the reservoir or plurality of microcapsules as explained above. The active agent may be present either alone or in combination with other active agents and/or a pharmaceutically acceptable carrier. Some suitable carriers are disclosed in U.S. Pat. No. 3,996,934 and include, for example, sterile water; saline; dextrose; dextrose in water or saline; condensation products of castor oil and ethylene oxide combining about 30 to about 35 moles of ethylene oxide per mole of castor oil; liquid glyceryl triesters of a lower molecular weight fatty acid; lower alkanols; oils such as corn oil, peanut oil, sesame oil and the like, with emulsifiers such as mono- or diglyceride of a fatty acid, or a phosphatide, e.g. lecithin, and the like; glycols; polyalkylene glycols; aqueous media in the presence of a suspending agent, for example, sodium carboxymethyl cellulose; sodium alginate; poly(vinylpyrrolidone); and the like, either alone or with suitable dispensing agents such as lecithin, polyoxyethylene stearate and the like. The carrier may also contain adjuvants such as preserving, stabilizing, wetting and emulsifying agents, and the like.

The active agent, whether in the presence of absence of a carrier, may also be combined in the reservoir or plurality of microcapsules with a transporting agent which assists the drug delivery device to achieve the administration of a drug to a receptor such as by enhancing penetration through the skin. Some transporting agents suitable for use in the present invention include those described in U.S. Pat. No. 3,996,934. Suitable transporting agents include monovalent, saturated and unsaturated aliphatic, cycloaliphatic and aromatic alcohols having 4 to 12 carbon atoms, such as hexanol, cyclohexanol and the like; aliphatic, cycloaliphatic and aromatic hydrocarbons having from 5 to 12 carbon atoms such as hexane, cyclohexane, isopropylbenzene and the like; cycloaliphatic and aromatic aldehydes and ketones having from 4 to 10 carbon atoms such as cyclohexanone; acetamide; N,N-di(lower alkyl)acetamides such as N,N-diethyl acetamide, N,N-dimethyl acetamide, and the like; N-(2-hydroxyethyl)acetamide; and other transporting agent such as aliphatic, cycloaliphatic and aromatic esters; N,N-di-lower alkyl sulfoxides; essential oils; halogenated or nitrated aliphatic, cycloaliphatic and aromatic hydrocarbons; salicylates; polyalkylene glycol silicates; mixtures of the above materials; and the like.

For example, U.S. Pat. No. 4,031,894 discloses droplets of scopolamine dispersed in a gelled mixture of mineral oil and a blend of polyisobutene. These oil-polyisobutene mixtures are excellent adhesives and help to hold the bandage together. The good adhesive property is advantageous in maintaining the structural integrity of the device without the requirement of heat sealing the layers together.

In addition, U.S. Pat. No. 3,742,951 discloses a reservoir of nitroglycerin in a gel of propylene glycol and carboxy vinyl resin. Such reservoirs are also suitable in the present invention.

The host to which an active agent is administered by means of the inventive device may be any host on which a drug or other active agent has the desired effect. The host may be, for example, a mammal such as a human being, or, for that matter, any warm blooded or cold blooded animal. The advantage of administering the active agent may be therapeutic or experimental. The device of this invention may also be for any other advantageous purpose.

In a preferred embodiment, the device contains a protective liner attached to the device at the surfaces of the impermeable adhesive layer and the permeable adhesive layer to be adhered to the skin or mucosa. The protective liner may be made of the same materials suitable for use in the outer surface member as discussed above. Such material is preferably made removable or releasable from the adhesive layers by, for example, treatment with silicone or other suitable coating. The removal of the device from the protective liner may also be provided by mechanical treatment of the protective liner, e.g., by embossing the protective liner.

The degree of impermeability (for the impermeable adhesive and for that matter the other elements of the device which are desired to be impermeable to the active agent) is that degree which prevents the active agent and/or the permeable adhesive from permeating or oozing away from the device during normal periods of storage and use. The device preferably remains therapeutically effective for at least 2 years, more preferably at least 5 years, and most preferably at least 10 years.

The distribution of the active agent between the permeable adhesive (p) and impermeable adhesive (i) may be defined in terms of flux (J) wherein: J=DC/A, C represents the solubility of the active agent in an adhesive layer, D represents the diffusion coefficient for the active agent in the adhesive, and A represents the width of the layer. Therefore:

$$J_i/J_p = D_i C_i A_p / D_p C_p A_i = K_D K_C K^{-1}{}_A.$$

Optimally, $J_i/J_p$ is 0. To the extent that the active agent is less compatable with the impermeable adhesive than with the permeable adhesive, $J_i/J_p$ will be less than 1. Preferably, $J_i/J_p$ will be less than 0.5 and more preferably less than 0.1.

The device of the present invention may be made by methods conventional in the art. Some suitable methods are described in U.S. Pat. Nos. 3,734,097; 3,996,934; and 4,031,894. In a preferred embodiment of the present invention, the device is of a "ravioli" type, i.e., it includes an overlay covering layer, e.g., as shown in FIG. 1. In this instance, the overlay covering layer is applied to the outer surface of the backing member, e.g., as shown in FIG. 1, the protective liner is applied, and the device is then die cut by processes well-known in the labeling field.

The device of the present invention is used in the same manner as those devices which are conventional in the prior art. In most instances, a protective, releaseable liner attached to the skin-side surface of the impermeable and permeable adhesive layers of the device is removed and such surface of the permeable and impermeable adhesive layers is applied to the desired area of the skin or mucosa.

The following examples are presented to illustrate the practice of the invention and are not intended as an indication of the limits of the scope thereof.

EXAMPLE 1

A typical device in accordance with the present invention can be prepared from a backing member of aluminized polyethylene terephthalate film that is impermeable to nitroglycerine; a drug reservoir containing nitroglycerine adsorbed on lactose, colloidal silicon dioxide and silicone medical fluid; a ethylene/vinyl acetate copolymer membrane containing 9% by weight vinyl acetate that is permeable to nitroglycerine; and a layer of hypoallergenic silicone (permeable) adhesive which is also permeable to the nitroglycerine. The drug reservoir is contained by the backing member and the semi-permeable EVA membrane, which is sealed to the backing member. The permeable adhesive is applied to the outer surface of the semi-permeable membrane. An overlay covering layer can be prepared of a polyvinyl chloride film which can be coated on one surface with a cross linking acrylic pressure sensitive adhesive (impermeable adhesive). The adhesive-coated side of the overlay covering layer is applied to the outer surface of the backing member. The overlay covering layer is of a shape and surface area so that the overlay covering layer completely overlaps the backing member and thus the other elements discussed above. Thus, the impermeable adhesive layer on the face of the device to be applied to the skin or mucosa surrounds the perimeter of the permeable adhesive layer. A protective liner comprised of a silicone release coated polyethylene terephthalate film is applied to the surface of the device containing the permeable and impermeable adhesive layers. The device is cut through the overlay covering layer/impermeable adhesive layer/protective liner portion to provide the desired shape. The nitroglycerine in this device is contained within an impermeable pocket created by the overlay covering layer, the impermeable adhesive layer and the protective liner. The device is employed by removing the protective liner and applying the adhesive side of the device to the skin, e.g., the chest area.

EXAMPLE 2

A device in accordance with the present invention for transdermal administration of scopolamine can be prepared from a backing member of aluminized polyethylene terephthalate film that is impermeable to scopolamine; a drug reservoir of scopolamine, mineral oil, and polyisobutylene; a microporous polypropylene membrane; and an adhesive formulation of mineral oil, polyisobutylene and scopolamine (permeable adhesive). An overlay covering layer can be prepared of a polyurethane film which can be coated on one surface with a cross linking acrylic pressure sensitive adhesive (impermeable adhesive). The adhesive-coated side of the overlay covering layer is applied to the outer surface of the backing member. The overlay covering layer is of a shape and surface area so that the overlay covering layer completely overlaps the backing member and thus the other elements discussed above. Thus, the impermeable adhesive layer in the face of the device to be applied to the skin surrounds the perimeter of the permeable adhesive layer. A protective liner comprised of a silicone release coated polyethylene terephthalate film is applied to the surface of the device containing the permeable and impermeable adhesive layers. The device is cut through the overlay covering layer/impermeable adhesive layer/protective liner portion to provide the desired shape. The scopolamine is contained in the device within an impermeable pocket created by the overlay covering layer, the impermeable adhesive layer and the protective liner. The device is employed by removing the protective liner and applying the adhesive side of the device to the skin.

EXAMPLE 3

A "dummy" device in accordance with the present invention was prepared with a backing member composed of a combination film of polyethylene and polyethylene terephthlate. This film was heat sealed to a ethylene vinyl acetate membrane about the periphery of the membrane to form a reservoir between the membrane and the backing member. A polyisobutylene adhesive (permeable adhesive layer) was applied to the exterior surface of the membrane. An overlay covering layer consisting of polyethylene film was coated with a cross linking acrylic pressure sensitive adhesive. This adhesive-coated overlay covering layer was cut into a shape and size so that, when it was applied to the exterior surface of the backing member, it overlapped completely the backing member and thus the reservoir membrane and the permeable adhesive layer. The overlay covering layer was applied to the backing member in this manner so that the impermeable adhesive layer on the surface of the device to be applied to the skin completely surrounded the perimeter of the permeable adhesive layer. A silicone release coated polyethylene terephthlate film was applied to the exterior surface of the impermeable and permeable adhesive layers and the device was cut to the desired shape by cutting only through the area of the overlay covering/impermeable adhesive layer/protective liner.

It will be understood that the embodiments described herein are merely exemplary and that a person skilled in the art may make many variations and modifications without departing from the spirit and scope of the invention. All such modifications and variations are intended to be included within the scope of the invention as described in the appended claims.

What is claimed is:

1. A device for the administration of an active agent to the skin or mucosa of a host comprising a reservoir containing said active agent, said reservoir including an inner surface and an outer surface, an active agent permeable membrane layer formed on said inner surface of said reservoir, said active agent permeable membrane layer including an outer surface facing said reservoir and an inner surface, an active agent impermeable barrier layer formed on said outer surface of said reservoir, so that said reservoir is completely enclosed between said active agent permeable membrane layer and said active agent impermeable barrier layer, said active agent impermeable barrier layer having an inner surface facing said reservoir and an outer surface, and extending peripherally beyond said reservoir about the entire periphery thereof so as to create an extended peripheral area of said active agent impermeable barrier layer, an active agent impermeable adhesive layer applied to said inner surface of said extended peripheral area of said active agent impermeable barrier layer, and an active agent permeable adhesive layer applied to said inner surface of said active agent permeable membrane layer, whereby substantially the entire inner surface of said device contains either said active agent impermeable adhesive layer or said active agent permeable adhesive layer, each of said active agent impermeable adhesive layer and said active agent permeable adhesive layer being adopted to adhere to the skin or mucosa of said host so as to permit said device to be firmly adhered thereto, whereby active agent can be released through said active agent permeable membrane layer and said active agent permeable adhesive layer to said skin or mucosa to provide a continuous dose of said active agent thereto, but cannot permeate through said active agent impermeable barrier layer or radially outward through said active agent impermeable adhesive layer.

2. The device of claim 1, wherein said active agent impermeable barrier layer comprises a cover layer including an inner surface and an outer surface, and wherein said active agent impermeable adhesive layer is applied to substantially the entire inner surface of said cover layer.

3. The device of claim 1, wherein said active agent impermeable barrier layer includes a backing member disposed on said portion of said inner surface of said active agent impermeable barrier layer corresponding to said reservoir.

4. The device of claim 2, wherein said active agent impermeable barrier layer includes a backing member disposed on the portion of said active agent impermeable adhesive layer corresponding to said reservoir.

5. The device of claim 1, wherein said active agent impermeable barrier layer comprises a single layer.

6. The device of claim 1, wherein said active agent permeable membrane layer and said active agent permeable adhesive layer are monolithic.

7. The device of claim 1, including a protective liner releasably attached to said active agent permeable adhesive layer and said active agent impermeable adhesive layer so as to permit removal of said protective liner and application of said active agent impermeable adhesive layer and said active agent permeable adhesive layer to the skin or mucosa of said host.

8. The device of claim 7, wherein said active agent impremeable adhesive layer is not applied to the entire inner surface of said extended peripheral area of said active agent impermeable barrier layer, and said active agent impermeable barrier layer thus extends radially outwardly past said active agent impermeable adhesive layer to act as a tab for removal of said protective layer.

9. The device of claim 3, wherein said active agent permeable membrane layer extends peripherally beyond said reservoir so as to provide at least a portion of overlapping peripheral surfaces between said peripheral portion of said active agent permeable membrane layer and said peripheral portion of said active agent impermeable barrier layer, and wherein said overlapping peripheral portions are heat sealed together to create an active agent impermeable seal surrounding said reservoir, whereby said active agent impermeable adhesive layer is applied to said active agent impermeable seal.

10. The device of claim 1, wherein said active agent impermeable adhesive layer comprises an adhesive composition selected from the group consisting of natural rubber adhesive, acrylic adhesives, and synthetic adhesives.

11. The device of claim 1, wherein said active agent permeable adhesive layer comprises an adhesive selected from the group consisting of acrylate and methacrylate resins; copolymers of acrylate or methacrylate esters with acrylic acid, methacrylic acid, acrylamide, methacrylamides, N-alkoxymethyl acrylamides, N-alkoxymethyl methacrylamides, N-t-butylacrylamide, itaconic acid, vinylacetate, N-branched aklylm maleamic acids wherein the alkyl group has 10 to 24 carbon atoms, glycol diacrylates, or mixture of these monomers; silicon rubber; styrene-butadiene rubber; butylether rubber; neoprene rubber; nitrile rubber; polyisobutylene; polybutadiene; polyisoprene; polyurethane elastomers; polyvinyl alcohol; polyvinyl ethers; polyvinyl pyrrolidone; polyvinyl acetate; ureaformaldehyde resins; phenol formaldehyde resins; resorcinal formaldehyde resins; ethyl cellulose; methyl cellulose; nitrocellulose; cellulose acetate-butyrate; carboxymethyl cellulose; guar gum; acacia gum; pectina gum; starch; destria; gelatin; and casein.

12. The device of claim 1, wherein said active agent permeable membrane layer comprises a material selected from the group consisting of polypropylene, polycarbonates, polyvinyl chloride, cellulose acetate, cellulose nitrate and polyacrylonitrile.

13. The device of claim 1, wherein said active agent impermeable barrier layer comprises a material selected from the group consisting of cellophane, cellulose acetate, ethylcellulose, plasticized vinyl acetate-vinyl chloride copolymers, ethylene-vinyl acetate copolymer, polyethylene terephthalate, nylon, polyethylene, polypropylene, polyvinylidene chloride, paper, cloth and aluminum foil.

14. The device of claim 2 wherein said cover layer is selected from the group consisting of a film of polyethylene terephthalate on polyethylene or a polyethylene/metallized polyethylene terephthalate/polyethylene laminate.

15. The device of claim 1, wherein said active agent is selected from the group consisting of scopolamine, nitroglycerine and estradiol.

16. A device for the administration of an active agent to the skin or mucosa of a host comprising a reservoir containing said active agent, said reservoir including an inner surface and an outer surface, an active agent impermeable barrier layer formed on said outer surface of said reservoir, said active agent impermeable barrier layer having an inner surface facing said reservoir and an outer surface, and extending peripherally beyond said reservoir about the entire periphery thereof so as to create an extended peripheral area of said active agent impermeable barrier layer, an active agent impermeable adhesive layer applied to said inner surface of said extended peripheral area of said active agent impermeable barrier layer, said reservoir containing an active agent permeable adhesive layer containing a plurality of microcapsules therein, said microcapsules containing said active agent encapsulated by an active agent permeable membrane, whereby substantially the entire inner surface of said device contains either said active agent impermeable adhesive layer or said active agent permeable adhesive layer, each of said active agent impermeable adhesive layer and said active agent permeable adhesive layer being adapted to adhere to the skin or mucosa of said host so as to permit said device to be firmly adhered thereto, whereby active agent can be released through said active agent permeable membrane and said active agent permeable adhesive layer to said skin or mucosa to provide a continuous dose of said active agent thereto, but cannot permeate through said active agent impermeable barrier layer or radially outward through said active agent impermeable adhesive layer.

17. The device of claim 16, wherein said active agent impermeable barrier layer comprises a cover layer including an outer surface and an inner surface, and wherein said active agent impermeable adhesive layer is applied to substantially the entire inner surface of said cover layer.

18. The device of claim 16, wherein said active agent impermeable barrier layer includes a backing member disposed on said portion of said inner surface of said active agent impermeable barrier layer corresponding to said rerservoir.

19. The device of claim 17, wherein said active agent impermeable barrier layer includes a backing member disposed on the portion of said active agent impermeable adhesive layer corresponding to said reservoir.

20. The device of claim 16, wherein said active agent impermeable barrier layer comprises a single layer.

21. The device of claim 16, wherein said active agent impermeable adhesive layer comprises an adhesive composition selected from the group consisting of natural rubber adhesives, acrylic adhesives, and synthetic adhesives.

22. The device of claim 16, wherein said active agent permeable adhesive layer comprises an adhesive selected from the group consisting of acrylate and methacrylate resins; copolymers of acrylate or methacrylate esters with acrylic acid, methacrylic acid, acrylamide, methacrylamides, N-alkoxymethyl acrylamides, N-alkoxymethyl methacrylamides, N-t-butylacrylamide, itaconic acid, vinylacetate, N-branched aklylm maleamic acids wherein the alkyl group has 10 to 24 carbon atoms, glycol diacrylates, or mixture of these monomers; silicon rubber; styrene-butadiene rubber; butyl-ether rubber; neoprene rubber; nitrile rubber; polyisobutylene; polybutadiene; polyisoprene; polyurethane elastomers; polyvinyl alcohol; polyvinyl ethers; polyvinyl pyrrolidone; polyvinyl acetate; ureaformaldehyde resins; phenol formaldehyde resins; resorcinal formaldehyde resins; ethyl cellulose; methyl cellulose; nitrocellulose; cellulose acetate-butyrate; carboxymethyl cellulose; guar gum; acacia gum; pectina gum; starch; destria; gelatin; and casein.

23. The device of claim 16, wherein said active agent permeable membrane layer is selected from the group consisting of polyvinyl chloride either unplasticized or plasticized with long-chain fattyamides, plasticized nylon, unplaticized soft nylon, silicone rubber, polyethylene, polyethylene terephthalate, polymerized esters of scrylic and methacrylic acide, modified collagent, cross-linked hydrophilic polyether gels, cross-linked vpolyvinyl alcohol, cross-linked partially hydrolyzed polyvinyl acetate, methyl cellulose, ethyl cellulose, hydroxyethyl cellulose, acacia gum, carboxymethyl cellulose, and carageenan alone or combined with gelatin.

24. The device of claim 17, wherein said cover layer is selected from the group consisting of a film of polyethylene terephthalate on polyethylene or a polyethylene/metallized polyethylene terephthalate/polyethylene laminate.

25. The device of claim 16, wherein said active agent is selected form the group consisting of scopolamine, nitroglycerine and estradiol.

* * * * *